United States Patent
Viengkham et al.

(10) Patent No.: US 12,096,896 B2
(45) Date of Patent: Sep. 24, 2024

(54) AUTONOMOUS SPACE STERILIZATION OF AIR AND FLOOR WITH CONTAMINATION INDEX

(71) Applicant: Honeywell International Inc., Charlotte, NC (US)

(72) Inventors: Manyphay Viengkham, Cumming, GA (US); Sunil Job, Bangalore (IN)

(73) Assignee: Honeywell International Inc., Charlotte, NC (US)

( * ) Notice: Subject to any disclaimer, the term of this patent is extended or adjusted under 35 U.S.C. 154(b) by 430 days.

(21) Appl. No.: 17/557,634

(22) Filed: Dec. 21, 2021

(65) Prior Publication Data

US 2022/0192454 A1    Jun. 23, 2022

Related U.S. Application Data

(60) Provisional application No. 63/129,290, filed on Dec. 22, 2020.

(51) Int. Cl.
| | |
|---|---|
| *A47L 11/40* | (2006.01) |
| *A61L 2/24* | (2006.01) |

(Continued)

(52) U.S. Cl.
CPC ............. *A47L 11/4011* (2013.01); *A61L 2/24* (2013.01); *A61L 9/20* (2013.01); *G05D 1/0219* (2013.01);

(Continued)

(58) Field of Classification Search
CPC ............. A47L 11/4011; A47L 2201/04; A47L 2201/06; A47L 9/12; A47L 9/281;

(Continued)

(56) References Cited

U.S. PATENT DOCUMENTS 8,774,970 B2 *   7/2014  Knopow ............... A47L 5/28
                                                   15/385
8,786,429 B2 *   7/2014  Li ........................ G08B 21/245
                                                   205/687

(Continued)

FOREIGN PATENT DOCUMENTS

| CN | 106196325 A | 12/2016 |
|---|---|---|
| KR | 20190134973 A | 12/2019 |
| KR | 20200035391 A | 4/2020 |

OTHER PUBLICATIONS

EP Office Action Mailed on Jul. 14, 2023 for EP Application No. 21217027, 9 page(s).

(Continued)

*Primary Examiner* — Bhavesh V Amin
(74) *Attorney, Agent, or Firm* — Alston & Bird LLP

(57) ABSTRACT

A method is disclosed that includes continuously obtaining air purity and floor particle data from one or more sensors and/or one or more cameras of a robotic device among a fleet of robotic devices; determining whether air impurities around the robotic device exceed an air purity threshold based on air purity feedback from the one or more sensors of the robotic device; based on the determination whether air impurities around the robotic device exceed the air purity threshold, modifying an air purification mode of the robotic device; determining whether floor particles around the robotic device exceed a floor particle threshold based on floor particle feedback from the one or more sensors of the robotic device; and based on the determination whether floor particles around the robotic device exceed the floor particle threshold, modifying a floor cleaning mode of the robotic device.

20 Claims, 9 Drawing Sheets

(51) Int. Cl.
*A61L 9/20* (2006.01)
*G05D 1/00* (2024.01)

(52) U.S. Cl.
CPC ........ *G05D 1/0291* (2013.01); *A47L 2201/04* (2013.01); *A47L 2201/06* (2013.01); *A61L 2202/14* (2013.01); *A61L 2202/16* (2013.01); *A61L 2202/25* (2013.01); *A61L 2209/111* (2013.01)

(58) Field of Classification Search
CPC ...... A47L 2201/00; A47L 11/00; A47L 11/40; A47L 11/4002; A61L 2/24; A61L 9/20; A61L 2202/14; A61L 2202/16; A61L 2202/25; A61L 2209/111; G05D 1/0219; G05D 1/0291; Y02B 30/70; F24F 2110/64; F24F 2110/65; F24F 11/54; F24F 11/56; F24F 11/65; F24F 11/89; F24F 8/10; F24F 2221/42; F24F 8/20; F24F 11/64
See application file for complete search history.

(56) References Cited

U.S. PATENT DOCUMENTS

| | | | | |
|---|---|---|---|---|
| 10,830,461 | B2* | 11/2020 | Xing | B01D 53/06 |
| 10,932,641 | B2* | 3/2021 | Erkek | F24F 8/10 |
| 11,176,813 | B2* | 11/2021 | Rakshit | G08G 1/0116 |
| 11,460,859 | B2* | 10/2022 | Arnold | A47L 9/2826 |
| 11,465,085 | B2* | 10/2022 | Kang | B01D 46/4245 |
| 11,471,813 | B2* | 10/2022 | Kim | A47L 9/2805 |
| 11,471,814 | B2* | 10/2022 | Jones | A47L 9/102 |
| 11,497,372 | B2* | 11/2022 | Kang | F24F 11/89 |
| 11,571,648 | B2* | 2/2023 | Kim | A47L 9/2852 |
| 11,793,379 | B2* | 10/2023 | Jones | A47L 7/04 |
| 2002/0095239 | A1* | 7/2002 | Wallach | G05D 1/0295 |
| | | | | 700/245 |
| 2005/0207951 | A1* | 9/2005 | Lee | A61L 9/015 |
| | | | | 422/186.07 |
| 2006/0064204 | A1* | 3/2006 | Kim | G05D 1/0274 |
| | | | | 700/276 |
| 2008/0206092 | A1* | 8/2008 | Crapser | A61L 9/127 |
| | | | | 422/123 |
| 2012/0125363 | A1* | 5/2012 | Kim | A47L 9/2852 |
| | | | | 134/6 |
| 2014/0207280 | A1* | 7/2014 | Duffley | G05D 1/0016 |
| | | | | 700/257 |
| 2014/0207281 | A1* | 7/2014 | Angle | B25J 13/006 |
| | | | | 700/257 |
| 2014/0207282 | A1* | 7/2014 | Angle | H04L 12/2809 |
| | | | | 901/1 |
| 2015/0256355 | A1* | 9/2015 | Pera | H04L 12/2816 |
| | | | | 700/90 |
| 2016/0183752 | A1* | 6/2016 | Morin | A47L 9/127 |
| | | | | 15/340.1 |
| 2016/0334800 | A1* | 11/2016 | Han | G05D 1/0274 |
| 2017/0112344 | A1* | 4/2017 | Koura | A47L 11/4041 |
| 2017/0203446 | A1* | 7/2017 | Dooley | H04N 23/631 |
| 2018/0055312 | A1* | 3/2018 | Jung | G06T 19/006 |
| 2018/0055326 | A1* | 3/2018 | Jung | G06T 19/006 |
| 2018/0279847 | A1* | 10/2018 | Park | A47L 9/2857 |
| 2018/0299899 | A1* | 10/2018 | Suvarna | A47L 9/2805 |
| 2018/0353044 | A1* | 12/2018 | Erkek | G05D 1/0238 |
| 2018/0360282 | A1* | 12/2018 | Erkek | A47L 9/2847 |
| 2018/0360285 | A1* | 12/2018 | Erkek | A47L 9/28 |
| 2018/0364661 | A1* | 12/2018 | Hackert | A47J 43/07 |
| 2018/0372330 | A1* | 12/2018 | Ronda | F24C 7/08 |
| 2019/0056126 | A1* | 2/2019 | Law | F24F 11/58 |
| 2020/0003447 | A1* | 1/2020 | Lee | F24F 11/64 |
| 2020/0016524 | A1* | 1/2020 | Kim | B01D 46/0052 |
| 2020/0077861 | A1* | 3/2020 | Kwak | A47L 11/4061 |
| 2020/0100639 | A1* | 4/2020 | Ullmann | G05B 19/19 |
| 2021/0331112 | A1* | 10/2021 | Kim | B01D 46/4227 |
| 2021/0356158 | A1* | 11/2021 | Kwon | F24F 11/0001 |
| 2022/0042694 | A1* | 2/2022 | He | F24F 11/30 |
| 2022/0192454 | A1* | 6/2022 | Viengkham | G05D 1/0219 |
| 2022/0304529 | A1* | 9/2022 | Jones | A47L 9/28 |

OTHER PUBLICATIONS

European search report Mailed on May 11, 2022 for EP Application No. 21217027, 11 page(s).
EP Office Action Mailed on May 17, 2024 for EP Application No. 21217027, 11 page(s).

* cited by examiner

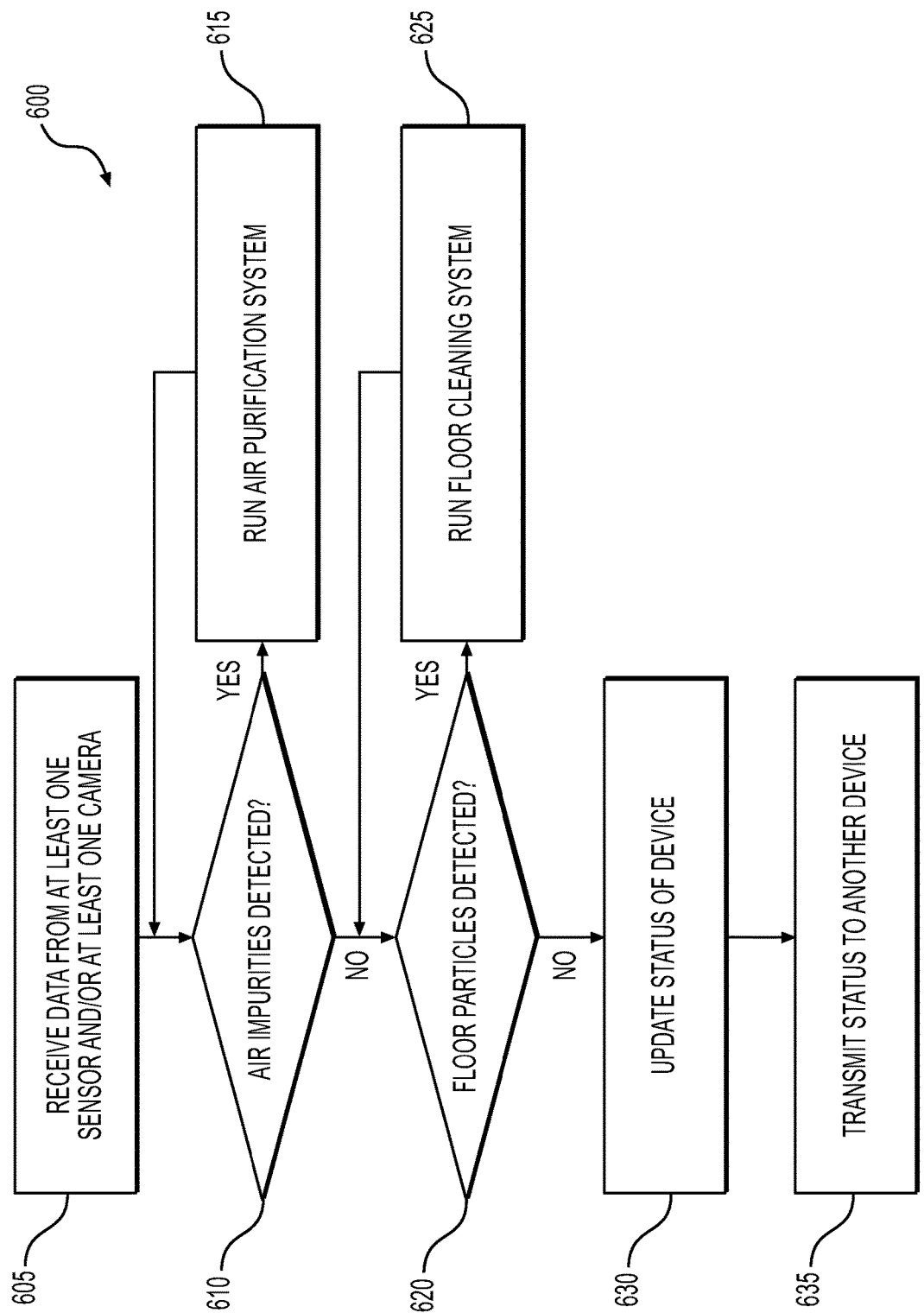

AUTONOMOUS SPACE STERILIZATION OF AIR AND FLOOR WITH CONTAMINATION INDEX

RELATED APPLICATIONS

This application claims the benefit of priority to U.S. Provisional Application No. 63/129,290, filed Dec. 22, 2020, which is incorporated herein by reference in its entirety.

FIELD

Various embodiments of the present disclosure relate generally to systems and methods for sterilization of air and floor, and more particularly, systems and methods for autonomous sterilization of air and floor using one or more network-connected robotic devices.

SUMMARY

According to certain aspects of the present disclosure, systems and methods are disclosed for autonomous sterilization of air and floor with a contamination index.

A method, includes: continuously obtaining air purity and floor particle data from one or more sensors and/or one or more cameras of a robotic device among a fleet of robotic devices; determining whether air impurities around the robotic device exceed an air purity threshold based on air purity feedback from the one or more sensors of the robotic device; based on the determination whether air impurities around the robotic device exceed the air purity threshold, modifying an air purification mode of the robotic device; determining whether floor particles around the robotic device exceed a floor particle threshold based on floor particle feedback from the one or more sensors of the robotic device; based on the determination whether floor particles around the robotic device exceed the floor particle threshold, modifying a floor cleaning mode of the robotic device; and transmitting an operating status of the robotic device to another robotic device in the fleet of robotic devices based on a status of the air purification mode and a status of the floor cleaning mode of the robotic device.

A system, including: at least one processor; and at least one memory, the at least one processor: continuously obtaining air purity and floor particle data from one or more sensors and/or one or more cameras of a robotic device among a fleet of robotic devices; determining whether air impurities around the robotic device exceed an air purity threshold based on air purity feedback from the one or more sensors of the robotic device; based on the determination whether air impurities around the robotic device exceed the air purity threshold, modifying an air purification mode of the robotic device; determining whether floor particles around the robotic device exceed a floor particle threshold based on floor particle feedback from the one or more sensors of the robotic device; based on the determination whether floor particles around the robotic device exceed the floor particle threshold, modifying a floor cleaning mode of the robotic device; and transmitting an operating status of the robotic device to another robotic device in the fleet of robotic devices based on a status of the air purification mode and a status of the floor cleaning mode of the robotic device.

A non-transitory computer-readable medium storing instructions that, when executed by at least one processor, cause the processor to perform a method of: continuously obtaining air purity and floor particle data from one or more sensors and/or one or more cameras of a robotic device among a fleet of robotic devices; determining whether air impurities around the robotic device exceed an air purity threshold based on air purity feedback from the one or more sensors of the robotic device; based on the determination whether air impurities around the robotic device exceed the air purity threshold, modifying an air purification mode of the robotic device; determining whether floor particles around the robotic device exceed a floor particle threshold based on floor particle feedback from the one or more sensors of the robotic device; based on the determination whether floor particles around the robotic device exceed the floor particle threshold, modifying a floor cleaning mode of the robotic device; and transmitting an operating status of the robotic device to another robotic device in the fleet of robotic devices based on a status of the air purification mode and a status of the floor cleaning mode of the robotic device.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 6 depicts an exemplary method of operating a robotic device, according to an exemplary embodiment.

DETAILED DESCRIPTION OF EMBODIMENTS

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

In general, the present disclosure provides for an "Internet-of-Things" or "IoT" platform for enterprise performance management that uses real-time accurate models and visual analytics to deliver intelligent actionable recommendations for sustained peak performance of an enterprise or organization. In particular, the present disclosure provides an IoT platform for using autonomous robotic devices to provide real-time information about air quality and floor particles present in multiple environments (e.g., offices, buildings, hospitals, houses, apartments, etc.) and to provide active measures for the sterilization of the air and floor based on an analysis of the real-time information. The IoT platform is an extensible platform that is portable for deployment in any cloud or data center environment for providing an enterprise-wide, top to bottom view, displaying the status of processes, assets, people, and safety. Further, the IoT platform of the present disclosure supports end-to-end capability to execute digital twins against process data and to translate the output into actionable insights, as detailed in the following description. The present disclosure further provides a cloud system with a secure, scalable infrastructure for collecting, aggregating & storing data, allowing connected devices to communicate, offering/SaaS (Software as a Service) solution, IaaS/PaaS (Infrastructure as a Service/Platform as a Service), and/or data lakes.

Figure 1:
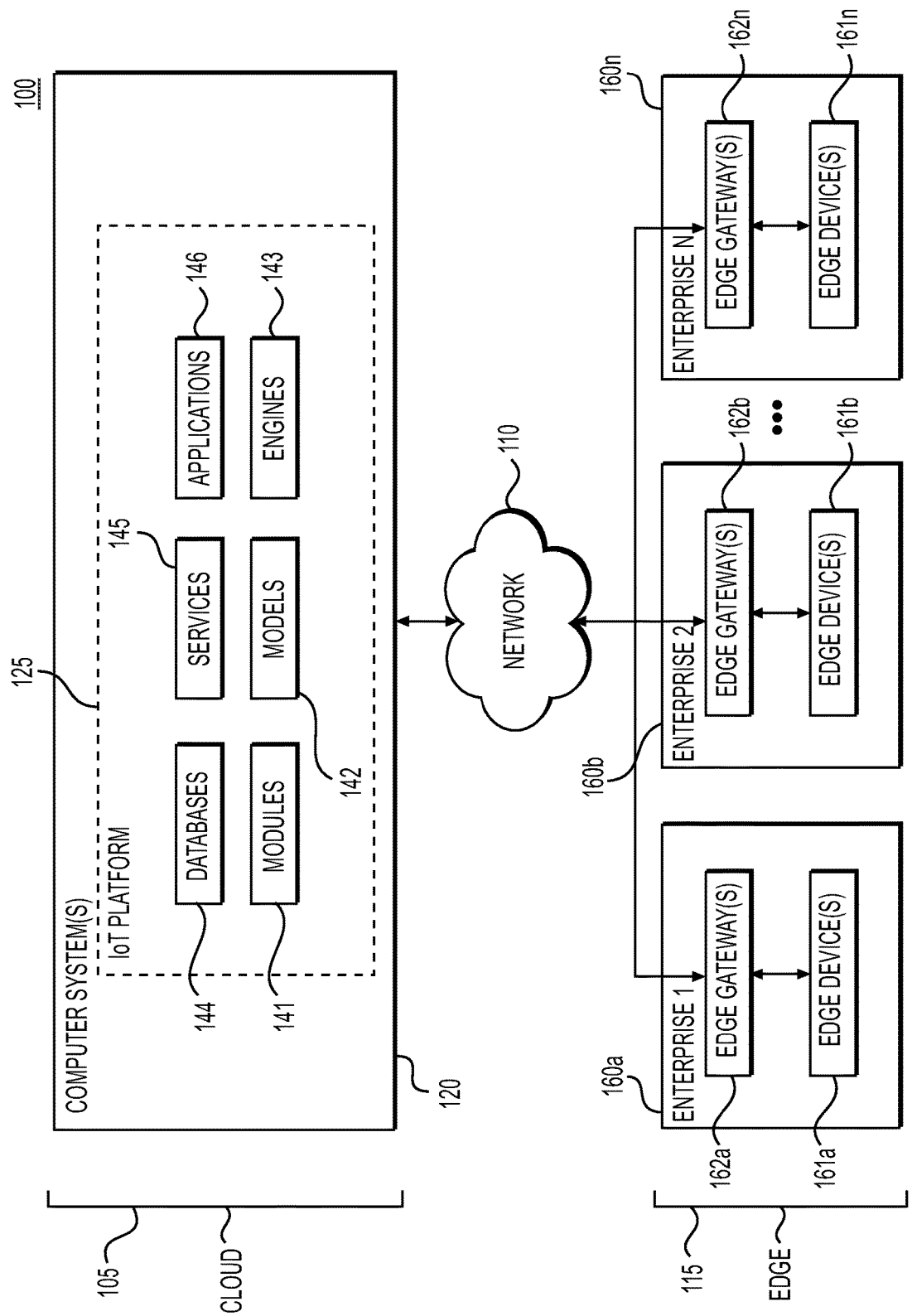
FIG. 1 depicts an exemplary networked computing system environment, according to one or more embodiments.

FIG. 1 illustrates an exemplary networked computing system environment 100, according to the present disclosure. As shown in FIG. 1, networked computing system environment 100 is organized into a plurality of layers including a cloud layer 105, a network layer 110, and an edge layer 115. As detailed further below, components of the edge 115 are in communication with components of the cloud 105 via network 110.

Network 110 may be any suitable network or combination of networks and may support any appropriate protocol suitable for communication of data to and from components of the cloud 105 and between various other components in the networked computing system environment 100 (e.g., components of the edge 115). Network 110 may include a public network (e.g., the Internet), a private network (e.g., a network within an organization), or a combination of public and/or private networks. Network 110 may be configured to provide communication between various components depicted in FIG. 1. Network 110 may comprise one or more networks that connect devices and/or components in the network layout to allow communication between the devices and/or components. For example, the network 110 may be implemented as the Internet, a wireless network, a wired network (e.g., Ethernet), a local area network (LAN), a Wide Area Network (WANs), Bluetooth, Near Field Communication (NFC), or any other type of network that provides communications between one or more components of the network layout. In some embodiments, network 110 may be implemented using cellular networks, satellite, licensed radio, or a combination of cellular, satellite, licensed radio, and/or unlicensed radio networks.

Components of the cloud 105 include one or more computer systems 120 that form a so-called "Internet-of-Things" or "IoT" platform 125. It should be appreciated that "IoT platform" is an optional term describing a platform connecting any type of Internet-connected device, and should not be construed as limiting on the types of computing systems useable within IoT platform 125. In particular, computer systems 120 may include any type or quantity of one or more processors and one or more data storage devices comprising memory for storing and executing applications or software modules of networked computing system environment 100. In one embodiment, the processors and data storage devices are embodied in server-class hardware, such as enterprise-level servers. For example, the processors and data storage devices may comprise any type or combination of application servers, communication servers, web servers, supercomputing servers, database servers, file servers, mail servers, proxy servers, and/virtual servers. Further, the one or more processors are configured to access the memory and execute processor-readable instructions, which when executed by the processors configures the processors to perform a plurality of functions of the networked computing system environment 100.

Computer systems 120 further include one or more software components of the IoT platform 125. For example, the software components of computer systems 120 may include one or more software modules to communicate with user devices and/or other computing devices through network 110. For example, the software components may include one or more modules 141, models 142, engines 143, databases 144, services 145, and/or applications 146, which may be stored in/by the computer systems 120 (e.g., stored on the memory), as detailed with respect to FIG. 2 below. The one or more processors may be configured to utilize the one or more modules 141, models 142, engines 143, databases 144, services 145, and/or applications 146 when performing various methods described in this disclosure.

Accordingly, computer systems 120 may execute a cloud computing platform (e.g., IoT platform 125) with scalable resources for computation and/or data storage, and may run one or more applications on the cloud computing platform to perform various computer-implemented methods described in this disclosure. In some embodiments, some of the modules 141, models 142, engines 143, databases 144, services 145, and/or applications 146 may be combined to form fewer modules, models, engines, databases, services, and/or applications. In some embodiments, some of the modules 141, models 142, engines 143, databases 144, services 145, and/or applications 146 may be separated into separate, more numerous modules, models, engines, databases, services, and/or applications. In some embodiments, some of the modules 141, models 142, engines 143, databases 144, services 145, and/or applications 146 may be removed while others may be added.

The computer systems 120 are configured to receive data from other components (e.g., components of the edge 115) of networked computing system environment 100 via network 110. Computer systems 120 are further configured to utilize the received data to produce a result. Information indicating the result may be transmitted to users via user computing devices over network 110. In some embodiments, the computer systems 120 may be referred to as a server system that provides one or more services including providing the information indicating the received data and/or the result(s) to the users. Computer systems 120 are part of an entity, which may include any type of company, organization, or institution that implements one or more IoT services. In some examples, the entity may be an IoT platform provider.

Components of the edge 115 include one or more enterprises 160a-160n each including one or more edge devices 161a-161n and one or more edge gateways 162a-162n. For example, a first enterprise 160a includes first edge devices 161a and first edge gateways 162a, a second enterprise 160b includes second edge devices 161b and second edge gateways 162b, and an nth enterprise 160n includes nth edge devices 161n and nth edge gateways 162n. As used herein, enterprises 160a-160n may represent any type of entity, facility, or vehicle, such as, for example, companies, divisions, buildings, manufacturing plants, warehouses, real estate facilities, laboratories, aircraft, spacecraft, automobiles, ships, boats, military vehicles, oil and gas facilities, or any other type of entity, facility, and/or vehicle that includes any number of local devices.

Figure 2:
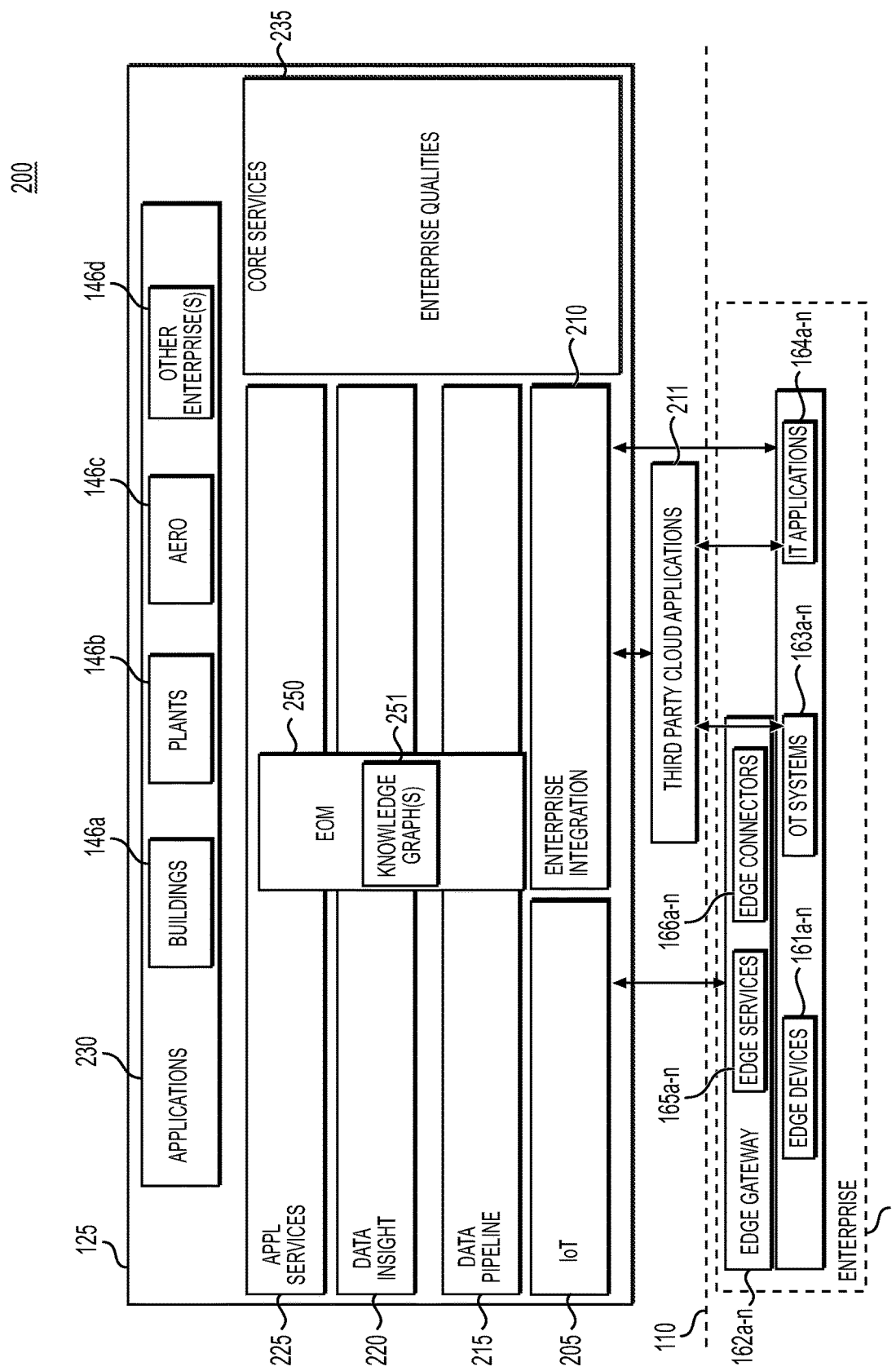
FIG. 2 depicts a schematic block diagram of a framework of an Internet-of-Things (IoT) platform of the networked computing system environment of FIG. 1.

The edge devices 161a-161n may represent any of a variety of different types of devices that may be found within the enterprises 160a-160n. Edge devices 161a-161n are any type of device configured to access network 110, or be accessed by other devices through network 110, such as via an edge gateway 162a-162n. Edge devices 161a-161n may be referred to in some cases as "IoT devices," which may therefore include any type of network-connected (e.g., Internet-connected) device. For example, the edge devices 161a-161n may include sensors, actuators, processors, computers, valves, pumps, ducts, vehicle components, cameras, displays, doors, windows, security components, HVAC components, factory equipment, and/or any other devices that may be connected to the network 110 for collecting, sending, and/or receiving information. Each edge device 161a-161n includes, or is otherwise in communication with, one or more controllers for selectively controlling a respective edge device 161a-161n and/or for sending/receiving information between the edge devices 161a-161n and the cloud 105 via network 110. With reference to FIG. 2, the edge 115 may also include operational technology (OT) systems 163a-163n and information technology (IT) applications 164a-164n of each enterprise 161a-161n. The OT systems 163a-163n include hardware and software for detecting and/or causing a change, through the direct monitoring and/or control of industrial equipment (e.g., edge devices 161a-161n), assets, processes, and/or events. The IT applications 164a-164n includes network, storage, and computing resources for the generation, management, storage, and delivery of data throughout and between organizations.

The edge gateways 162a-162n include devices for facilitating communication between the edge devices 161a-161n and the cloud 105 via network 110. For example, the edge gateways 162a-162n include one or more communication interfaces for communicating with the edge devices 161a-161n and for communicating with the cloud 105 via network 110. The communication interfaces of the edge gateways 162a-162n may include one or more cellular radios, Bluetooth, WiFi, near-field communication radios, Ethernet, or other appropriate communication devices for transmitting and receiving information. Multiple communication interfaces may be included in each gateway 162a-162n for providing multiple forms of communication between the edge devices 161a-161n, the gateways 162a-162n, and the cloud 105 via network 110. For example, communication may be achieved with the edge devices 161a-161n and/or the network 110 through wireless communication (e.g., WiFi, radio communication, etc.) and/or a wired data connection (e.g., a universal serial bus, an onboard diagnostic system, etc.) or other communication modes, such as a local area network (LAN), wide area network (WAN) such as the Internet, a telecommunications network, a data network, or any other type of network.

The edge gateways 162a-162n may also include a processor and memory for storing and executing program instructions to facilitate data processing. For example, the edge gateways 162a-162n can be configured to receive data from the edge devices 161a-161n and process the data prior to sending the data to the cloud 105. Accordingly, the edge gateways 162a-162n may include one or more software modules or components for providing data processing services and/or other services or methods of the present disclosure. With reference to FIG. 2, each edge gateway 162a-162n includes edge services 165a-165n and edge connectors 166a-166n. The edge services 165a-165n may include hardware and software components for processing the data from the edge devices 161a-161n. The edge connectors 166a-166n may include hardware and software components for facilitating communication between the edge gateway 162a-162n and the cloud 105 via network 110, as detailed above. In some cases, any of edge devices 161a-n, edge connectors 166a-n, and edge gateways 162a-n may have their functionality combined, omitted, or separated into any combination of devices. In other words, an edge device and its connector and gateway need not necessarily be discrete devices.

FIG. 2 illustrates a schematic block diagram of framework 200 of the IoT platform 125, according to the present disclosure. The IoT platform 125 of the present disclosure is a platform for enterprise performance management that uses real-time accurate models and visual analytics to deliver intelligent actionable recommendations for sustained peak performance of the enterprise 160a-160n. The IoT platform 125 is an extensible platform that is portable for deployment in any cloud or data center environment for providing an enterprise-wide, top to bottom view, displaying the status of processes, assets, people, and safety. Further, the IoT platform 125 supports end-to-end capability to execute digital twins against process data and to translate the output into actionable insights, using the framework 200, detailed further below.

As shown in FIG. 2, the framework 200 of the IoT platform 125 comprises a number of layers including, for example, an IoT layer 205, an enterprise integration layer 210, a data pipeline layer 215, a data insight layer 220, an application services layer 225, and an applications layer 230. The IoT platform 125 also includes a core services layer 235 and an extensible object model (EOM) 250 comprising one or more knowledge graphs 251. The layers 205-235 further include various software components that together form each layer 205-235. For example, each layer 205-235 may include one or more of the modules 141, models 142, engines 143, databases 144, services 145, applications 146, or combinations thereof. In some embodiments, the layers 205-235 may be combined to form fewer layers. In some embodiments, some of the layers 205-235 may be separated into separate, more numerous layers. In some embodiments, some of the layers 205-235 may be removed while others may be added.

The IoT platform 125 is a model-driven architecture. Thus, the extensible object model 250 communicates with each layer 205-230 to contextualize site data of the enterprise 160a-160n using an extensible object model (or "asset model") and knowledge graphs 251 where the equipment (e.g., edge devices 161a-161n) and processes of the enterprise 160a-160n are modeled. The knowledge graphs 251 of EOM 250 are configured to store the models in a central location. The knowledge graphs 251 define a collection of nodes and links that describe real-world connections that enable smart systems. As used herein, a knowledge graph 251: (i) describes real-world entities (e.g., edge devices 161a-161n) and their interrelations organized in a graphical interface; (ii) defines possible classes and relations of entities in a schema; (iii) enables interrelating arbitrary entities with each other; and (iv) covers various topical domains. In other words, the knowledge graphs 251 define large networks of entities (e.g., edge devices 161a-161n), semantic types of the entities, properties of the entities, and relationships between the entities. Thus, the knowledge graphs 251 describe a network of "things" that are relevant to a specific domain or to an enterprise or organization. Knowledge graphs 251 are not limited to abstract concepts and relations, but can also contain instances of objects, such as, for example, documents and datasets. In some embodiments, the knowledge graphs 251 may include resource description framework (RDF) graphs. As used herein, a "RDF graph" is a graph data model that formally describes the semantics, or meaning, of information. The RDF graph can also represent metadata (e.g., data that describes data). Knowledge graphs 251 can also include a semantic object model. The semantic object model is a subset of a knowledge graph 251 that defines semantics for the knowledge graph 251. For example, the semantic object model defines the schema for the knowledge graph 251.

As used herein, EOM 250 is a collection of application programming interfaces (APIs) that enables seeded semantic object models to be extended. For example, the EOM 250 of the present disclosure enables a customer's knowledge graph 251 to be built subject to constraints expressed in the customer's semantic object model. Thus, the knowledge graphs 251 are generated by customers (e.g., enterprises or organizations) to create models of the edge devices 161a-161n of an enterprise 160a-160n, and the knowledge graphs 251 are input into the EOM 250 for visualizing the models (e.g., the nodes and links).

The models describe the assets (e.g., the nodes) of an enterprise (e.g., the edge devices 161a-161n) and describe the relationship of the assets with other components (e.g., the links). The models also describe the schema (e.g., describe what the data is), and therefore the models are self-validating. For example, the model can describe the type of sensors mounted on any given asset (e.g., edge device 161a-161n) and the type of data that is being sensed by each sensor. A key performance indicator (KPI) framework can be used to bind properties of the assets in the extensible object model 250 to inputs of the KPI framework. Accordingly, the IoT platform 125 is an extensible, model-driven end-to-end stack including: two-way model sync and secure data exchange between the edge 115 and the cloud 105, metadata driven data processing (e.g., rules, calculations, and aggregations), and model driven visualizations and applications. As used herein, "extensible" refers to the ability to extend a data model to include new properties/columns/fields, new classes/tables, and new relations. Thus, the IoT platform 125 is extensible with regards to edge devices 161a-161n and the applications 146 that handle those devices 161a-161n. For example, when new edge devices 161a-161n are added to an enterprise 160a-160n system, the new devices 161a-161n will automatically appear in the IoT platform 125 so that the corresponding applications 146 can understand and use the data from the new devices 161a-161n.

In some cases, asset templates are used to facilitate configuration of instances of edge devices 161a-161n in the model using common structures. An asset template defines the typical properties for the edge devices 161a-161n of a given enterprise 160a-160n for a certain type of device. For example, an asset template of a pump includes modeling the pump having inlet and outlet pressures, speed, flow, etc. The templates may also include hierarchical or derived types of edge devices 161a-161n to accommodate variations of a base type of device 161a-161n. For example, a reciprocating pump is a specialization of a base pump type and would include additional properties in the template. Instances of the edge device 161a-161n in the model are configured to match the actual, physical devices of the enterprise 160a-160n using the templates to define expected attributes of the device 161a-161n. Each attribute is configured either as a static value (e.g., capacity is 1000 BPH) or with a reference to a time series tag that provides the value. The knowledge graph 251 can automatically map the tag to the attribute based on naming conventions, parsing, and matching the tag and attribute descriptions and/or by comparing the behavior of the time series data with expected behavior.

The modeling phase includes an onboarding process for syncing the models between the edge 115 and the cloud 105. For example, the onboarding process can include a simple onboarding process, a complex onboarding process, and/or a standardized rollout process. The simple onboarding process includes the knowledge graph 251 receiving raw model data from the edge 115 and running context discovery algorithms to generate the model. The context discovery algorithms read the context of the edge naming conventions of the edge devices 161a-161n and determine what the naming conventions refer to. For example, the knowledge graph 251 can receive "TMP" during the modeling phase and determine that "TMP" relates to "temperature." The generated models are then published. The complex onboarding process includes the knowledge graph 251 receiving the raw model data, receiving point history data, and receiving site survey data. The knowledge graph 251 can then use these inputs to run the context discovery algorithms. The generated models can be edited and then the models are published. The standardized rollout process includes manually defining standard models in the cloud 105 and pushing the models to the edge 115.

The IoT layer 205 includes one or more components for device management, data ingest, and/or command/control of the edge devices 161a-161n. The components of the IoT layer 205 enable data to be ingested into, or otherwise received at, the IoT platform 125 from a variety of sources. For example, data can be ingested from the edge devices 161a-161n through process historians or laboratory information management systems. The IoT layer 205 is in communication with the edge connectors 165a-165n installed on the edge gateways 162a-162n through network 110, and the edge connectors 165a-165n send the data securely to the IoT platform 205. In some embodiments, only authorized data is sent to the IoT platform 125, and the IoT platform 125 only accepts data from authorized edge gateways 162a-162n and/or edge devices 161a-161n. Data may be sent from the edge gateways 162a-162n to the IoT platform 125 via direct streaming and/or via batch delivery. Further, after any network or system outage, data transfer will resume once communication is re-established and any data missed during the outage will be backfilled from the source system or from a cache of the IoT platform 125. The IoT layer 205 may also include components for accessing time series, alarms and events, and transactional data via a variety of protocols.

The enterprise integration layer 210 includes one or more components for events/messaging, file upload, and/or REST/OData. The components of the enterprise integration layer 210 enable the IoT platform 125 to communicate with third party cloud applications 211, such as any application(s) operated by an enterprise in relation to its edge devices. For example, the enterprise integration layer 210 connects with enterprise databases, such as guest databases, customer databases, financial databases, patient databases, etc. The enterprise integration layer 210 provides a standard application programming interface (API) to third parties for accessing the IoT platform 125. The enterprise integration layer 210 also enables the IoT platform 125 to communicate with the OT systems 163a-163n and IT applications 164a-164n of the enterprise 160a-160n. Thus, the enterprise integration layer 210 enables the IoT platform 125 to receive data from the third party applications 211 rather than, or in combination with, receiving the data from the edge devices 161a-161n directly.

The data pipeline layer 215 includes one or more components for data cleansing/enriching, data transformation, data calculations/aggregations, and/or API for data streams. Accordingly, the data pipeline layer 215 can pre-process and/or perform initial analytics on the received data. The data pipeline layer 215 executes advanced data cleansing routines including, for example, data correction, mass balance reconciliation, data conditioning, component balancing and simulation to ensure the desired information is used as a basis for further processing. The data pipeline layer 215 also provides advanced and fast computation. For example, cleansed data is run through enterprise-specific digital twins. The enterprise-specific digital twins can include a reliability advisor containing process models to determine the current operation and the fault models to trigger any early detection and determine an appropriate resolution. The digital twins can also include an optimization advisor that integrates real-time economic data with real-time process data, selects the right feed for a process, and determines optimal process conditions and product yields.

The data pipeline layer 215 may also use models and templates to define calculations and analytics, and define how the calculations and analytics relate to the assets (e.g., the edge devices 161a-161n). For example, a pump template can define pump efficiency calculations such that every time a pump is configured, the standard efficiency calculation is automatically executed for the pump. The calculation model defines the various types of calculations, the type of engine that should run the calculations, the input and output parameters, the preprocessing requirement and prerequisites, the schedule, etc. The actual calculation or analytic logic may be defined in the template or it may be referenced. Thus, the calculation model can be used to describe and control the execution of a variety of different process models. Calculation templates can be linked with the asset templates such that when an asset (e.g., edge device 161a-161n) instance is created, any associated calculation instances are also created with their input and output parameters linked to the appropriate attributes of the asset (e.g., edge device 161a-161n).

The IoT platform 125 can support a variety of different analytics models including, for example, first principles models, empirical models, engineered models, user-defined models, machine learning models, built-in functions, and/or any other types of analytics models. Fault models and predictive maintenance models will now be described by way of example, but any type of models may be applicable.

Fault models are used to compare current and predicted enterprise 160a-160n performance to identify issues or opportunities, and the potential causes or drivers of the issues or opportunities. The IoT platform 125 includes rich hierarchical symptom-fault models to identify abnormal conditions and their potential consequences. For example, the IoT platform 125 can drill down from a high-level condition to understand the contributing factors, as well as determining the potential impact a lower level condition may have. There may be multiple fault models for a given enterprise 160a-160n looking at different aspects such as process, equipment, control, and/or operations. Each fault model can identify issues and opportunities in their domain, and can also look at the same core problem from a different perspective. An overall fault model can be layered on top to synthesize the different perspectives from each fault model into an overall assessment of the situation and point to the true root cause.

When a fault or opportunity is identified, the IoT platform 125 can make recommendations about the best corrective actions to take. Initially, the recommendations are based on expert knowledge that has been pre-programmed into the system by process and equipment experts. A recommendation services module presents this information in a consistent way regardless of source, and supports workflows to track, close out, and document the recommendation follow-up. The recommendation follow-up can be used to improve the overall knowledge of the system over time as existing recommendations are validated (or not) or new cause and effect relationships are learned by users and/or analytics.

The models can be used to accurately predict what will occur before it occurs and interpret the status of the installed base. Thus, the IoT platform 125 enables operators to quickly initiate maintenance measures when irregularities occur. The digital twin architecture of the IoT platform 125 can use a variety of modeling techniques. The modeling techniques can include, for example, rigorous models, fault detection and diagnostics (FDD), descriptive models, predictive maintenance, prescriptive maintenance, process optimization, and/or any other modeling technique.

The rigorous models can be converted from process design simulation. In this manner, process design is integrated with feed conditions and production requirement. Process changes and technology improvement provide business opportunities that enable more effective maintenance scheduling and deployment of resources in the context of production needs. The fault detection and diagnostics include generalized rule sets that are specified based on industry experience and domain knowledge and can be easily incorporated and used together with equipment models. The descriptive models identify a problem and then the predictive models can determine possible damage levels and maintenance options. The descriptive models can include models for defining the operating windows for the edge devices 161a-161n.

Predictive maintenance includes predictive analytics models developed based on rigorous models and statistic models, such as, for example, principal component analysis (PCA) and partial least square (PLS). Machine learning methods can be applied to train models for fault prediction. Predictive maintenance can leverage FDD-based algorithms to continuously monitor individual control and equipment performance. Predictive modeling is then applied to a selected condition indicator that deteriorates in time. Prescriptive maintenance includes determining what is the best maintenance option and when it should be performed based on actual conditions rather than time-based maintenance schedule. Prescriptive analysis can select the right solution based on the company's capital, operational, and/or other requirements. Process optimization is determining optimal conditions via adjusting set-points and schedules. The optimized set-points and schedules can be communicated directly to the underlying controllers, which enables automated closing of the loop from analytics to control.

The data insight layer 220 includes one or more components for time series databases (TDSB), relational/document databases, data lakes, blob, files, images, and videos, and/or an API for data query. When raw data is received at the IoT platform 125, the raw data can be stored as time series tags or events in warm storage (e.g., in a TSDB) to support interactive queries and to cold storage for archive purposes. Data can further be sent to the data lakes for offline analytics development. The data pipeline layer 215 can access the data stored in the databases of the data insight layer 220 to perform analytics, as detailed above.

The application services layer 225 includes one or more components for rules engines, workflow/notifications, KPI framework, BI, machine learning, and/or an API for application services. The application services layer 225 enables building of applications 146a-d. The applications layer 230 includes one or more applications 146a-d of the IoT platform 125. For example, the applications 146a-d can include a buildings application 146a, a plants application 146b, an aero application 146c, and other enterprise applications 146d. The applications 146 can include general applications 146 for portfolio management, asset management, autonomous control, and/or any other custom applications. Portfolio management can include the KPI framework and a flexible user interface (UI) builder. Asset management can include asset performance and asset health. Autonomous control can include energy optimization and predictive maintenance. As detailed above, the general applications 146 can be extensible such that each application 146 can be configurable for the different types of enterprises 160a-160n (e.g., buildings application 146a, plants application 146b, aero application 146c, and other enterprise applications 146d).

The applications layer 230 also enables visualization of performance of the enterprise 160a-160n. For example, dashboards provide a high-level overview with drill downs to support deeper investigations. Recommendation summaries give users prioritized actions to address current or potential issues and opportunities. Data analysis tools support ad hoc data exploration to assist in troubleshooting and process improvement.

The core services layer 235 includes one or more services of the IoT platform 125. The core services 235 can include data visualization, data analytics tools, security, scaling, and monitoring. The core services 235 can also include services for tenant provisioning, single login/common portal, self-service admin, UI library/UI tiles, identity/access/entitlements, logging/monitoring, usage metering, API gateway/dev portal, and the IoT platform 125 streams.

Figure 3A:
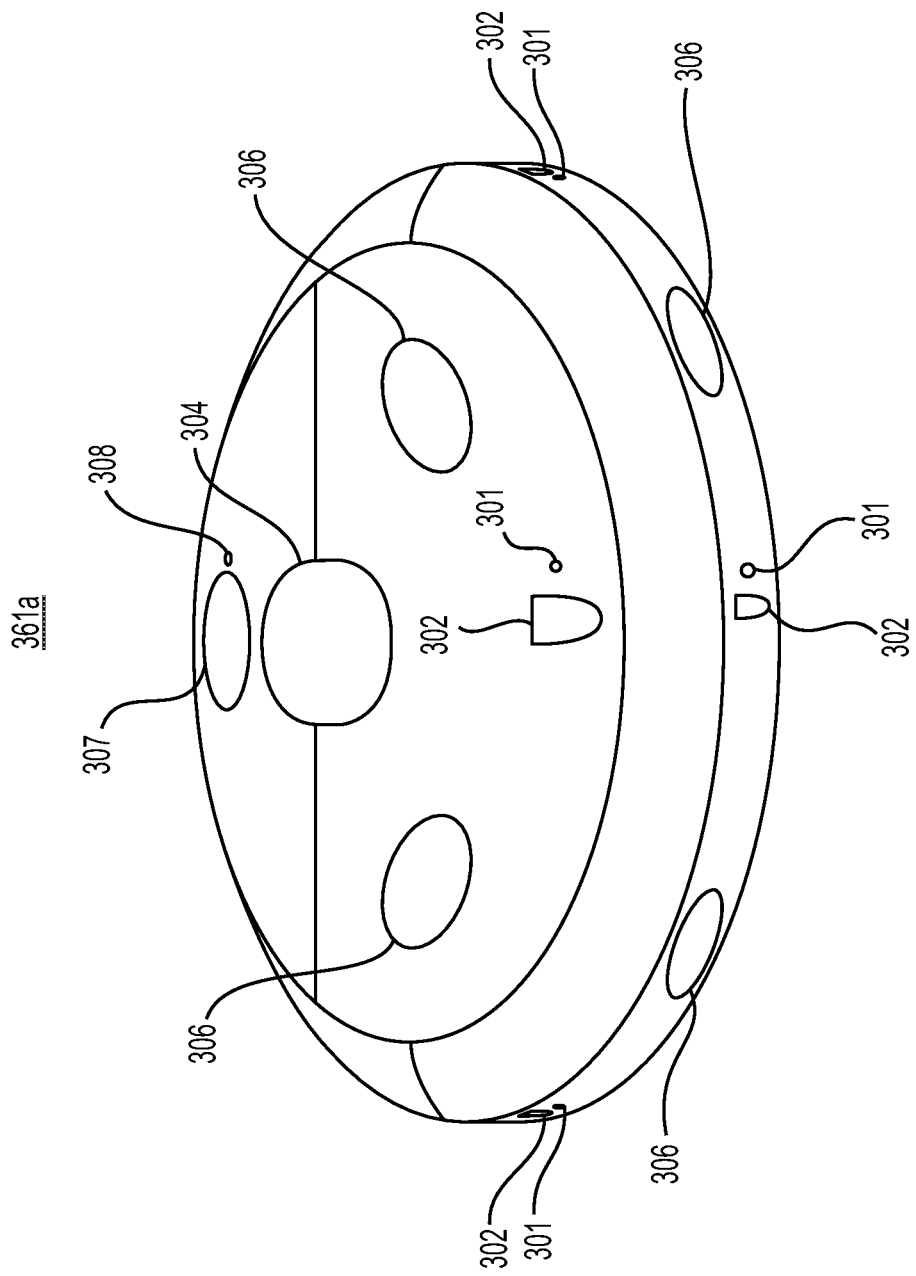
FIG. 3A depicts a top view of a robotic device that includes an air purification system and a vacuum system, according to an exemplary embodiment of the present disclosure.

FIG. 3A depicts a top view of a robotic device 361a that includes an air purification system and a vacuum system, according to an exemplary embodiment of the present disclosure. In one embodiment, the robotic device 361a is an edge device 161a, as described above with respect to FIGS. 1 and 2. The robotic device 361a may be a completely autonomous IoT device that connects with other devices through a wired network and/or wireless network (e.g., network 110). For example the robotic device 361a may connect to an IoT platform 125 formed by one or more computer systems 120 of cloud 105. As described above, the network 110 may be implemented as the Internet, a wireless network, a wired network (e.g., Ethernet), a local area network (LAN), a Wide Area Network (WANs), Bluetooth, Near Field Communication (NFC), or any other type of network that provides communications between one or more components of the network layout.

As illustrated in FIG. 3A, the robotic device 361a may include one or more sensors 301, one or more cameras 302, and an air filtration system 304. Each of the sensors 301 depicted in FIG. 3A may include one or more types of sensors. For example, the sensors 301 may be air quality sensors, proximity sensors, dust sensors, optical sensors, temperature sensors, pressure sensors, photosensors, air pollution sensors, weight measurement sensors, GPS sensors, and/or infrared sensors. The sensors 301 and cameras 302 may be used to identify characteristics of the surroundings of the robotic device 361a, enabling the device to navigate throughout an entire room and throughout multiple rooms in small and/or large buildings. Additionally, the robotic device 361a may include several ultraviolet C (UV-C) windows 306 through which UV-C light may be projected. For example, the robotic device may include one or more UV-C lamps which provide a disinfectant for air, water, and nonporous surfaces. when turned on, the UV-C lamps may provide a disinfectant by radiating light through the UV-C windows 306. The windows 306 may be designed as openings in the frame of the robotic device. Further, each of the windows may include a retractable non-transparent cover that may be open or closed independently of each other. The covers may be controlled manually and/or automatically by the robotic device 361a, based on which surfaces and/or areas are to be disinfected at any time. The openings may or may not be covered with a transparent material. The placement of the sensors 301, cameras 302, air filtration system 304, and UV-C windows 306 is not limited to the locations depicted in the drawings.

The robotic device may further include a display panel 307. The display panel provides key information such as device settings that may be seen from a distance. The robotic device may include an input button 308. The input button may be a mechanical button or may be activated through touch input.

The air filtration system 304 may use certified high-efficiency particulate air (HEPA) filters to purify any contaminated outside air. The air filtration system 304 may further include specialty air filters designed to neutralize several household odors, e.g., pet, kitchen, and smoking. Another specialty air filter is designed to reduce volatile organic compounds (VOCs) and neutralize fumes from renovation and home improvement products. A user may select which of the specialty air filters to use at any time. A VOC sensor may continuously monitor and provide real-time feedback on air quality using the display pan 307. For example, the display panel 307 may include a color-coded air quality indicator: a green indicator may be used to identify good air quality; a yellow indicator may be used to identify moderate air quality, and a red indicator may be used to identify poor air quality.

The air filtration system 304 may use certified HEPA filters to capture and eliminate up to 99.97 percent of harmful microscopic allergens, which may be as small as 0.3 microns, from the air that passes through the filters. Examples of allergens may include pollen, dust, pet dander, dust mite debris, and/or smoke particles, etc. The air purifiers may help reduce 99.9 percent of particular airborne viruses, bacteria and mold spores. In addition, the robotic device may include a carbon activated pre-filter that helps trap larger particles and helps reduce odors and VOCs.

Figure 3B:
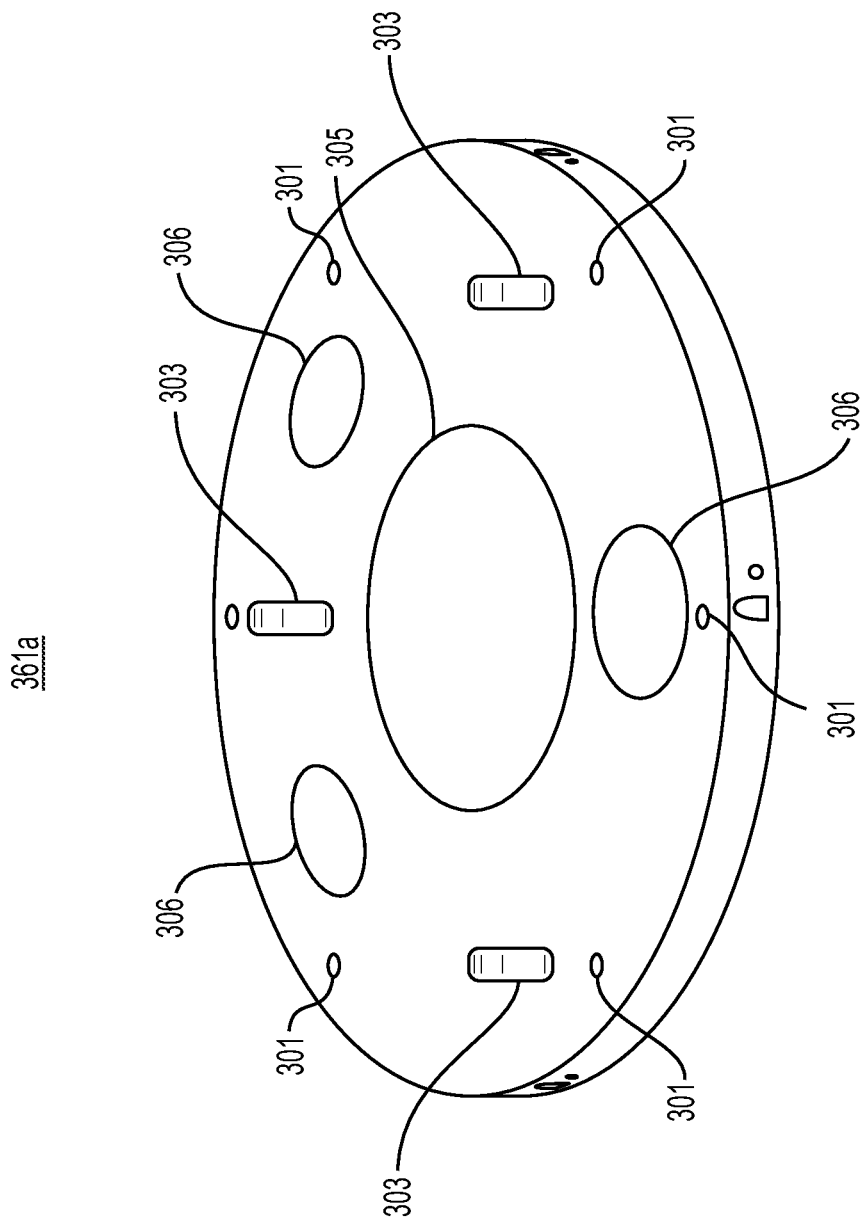
FIG. 3B depicts a bottom view of a robotic device, according to an exemplary embodiment of the present disclosure.

FIG. 3B depicts a bottom view of the robotic device 361a, according to an exemplary embodiment of the present disclosure. Each of the sensors 301 depicted in FIG. 3B may include one or more types of sensors. For example, the sensors 301 may be air quality sensors, proximity sensors, dust sensors, optical sensors, temperature sensors, pressure sensors, photosensors, air pollution sensors, and/or infrared sensors. As illustrated in FIG. 3B, the robotic device includes wheels 303. The wheels are controlled by a motor and the wheels 303 may swivel to allow for the robotic device 361a to move in all directions at all times. In one embodiment, the robotic device 361a includes a vacuum system 305 for cleaning floors and carpets. The vacuum system may include rotating brush and a filter. Additionally, the vacuum system may include a weight measurement sensor to determine an amount of dust and/or garbage that has been collected. All of the data collected by the sensors may be transferred to a centralized management system (e.g., cloud 105, BMS (building management system)) over a wired and/or wireless network (e.g., network 110).

Figure 4:
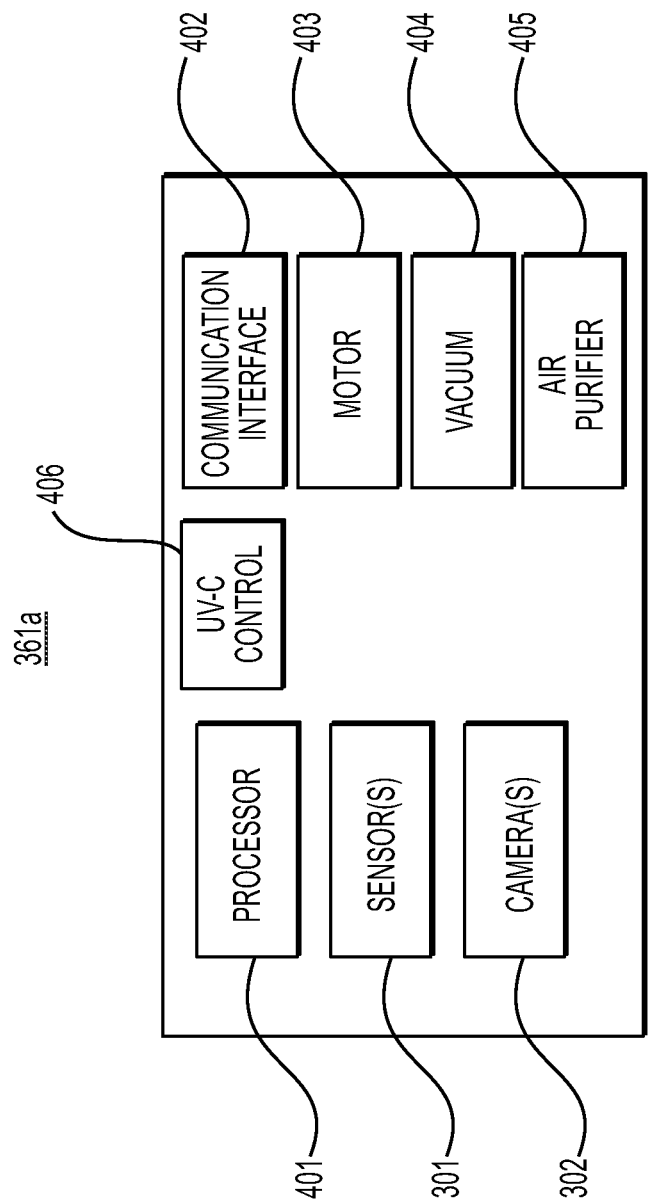
FIG. 4 depicts an exemplary block diagram of a robotic device, according to an exemplary embodiment of the present disclosure.

FIG. 4 depicts an exemplary block diagram of the robotic device 361a, according to an aspect of the disclosure. In one embodiment, the robotic device 361a includes a processor 401, a communication interface 402, motor(s) 403, a vacuum system 404, an air purification system 405, a UV-C control 406, one or more sensors 301 and/or one or more cameras 302. The communication interface includes capabilities for the robotic device 361a to communicate with other devices over a network 110, including communication with an external server and/or cloud 105. The network 110 may be implemented as the Internet, a wireless network, a wired network (e.g., Ethernet), a local area network (LAN), a Wide Area Network (WANs), Bluetooth, Near Field Communication (NFC), or any other type of network that provides communications between one or more components of the network layout. The one or more motors may control all aspects of the device, including the wheels 303, the vacuum system 404, and the air filtration system 405. The UV-C control 406 may control the operation of the UV-C lamps, which disinfect surfaces by radiating light through the UV-C windows 306

According to one embodiment, the communication interface 402 may connect to an augmented reality (AR) device, which allows a user to visualize the operation of the robotic device 361a and to view a simulation of various particles detected in the air. For example, the AR device will display the number of particles in the air based on the amount of impurities detected in the air by the sensors of the robotic device 361a.

Figure 5A:
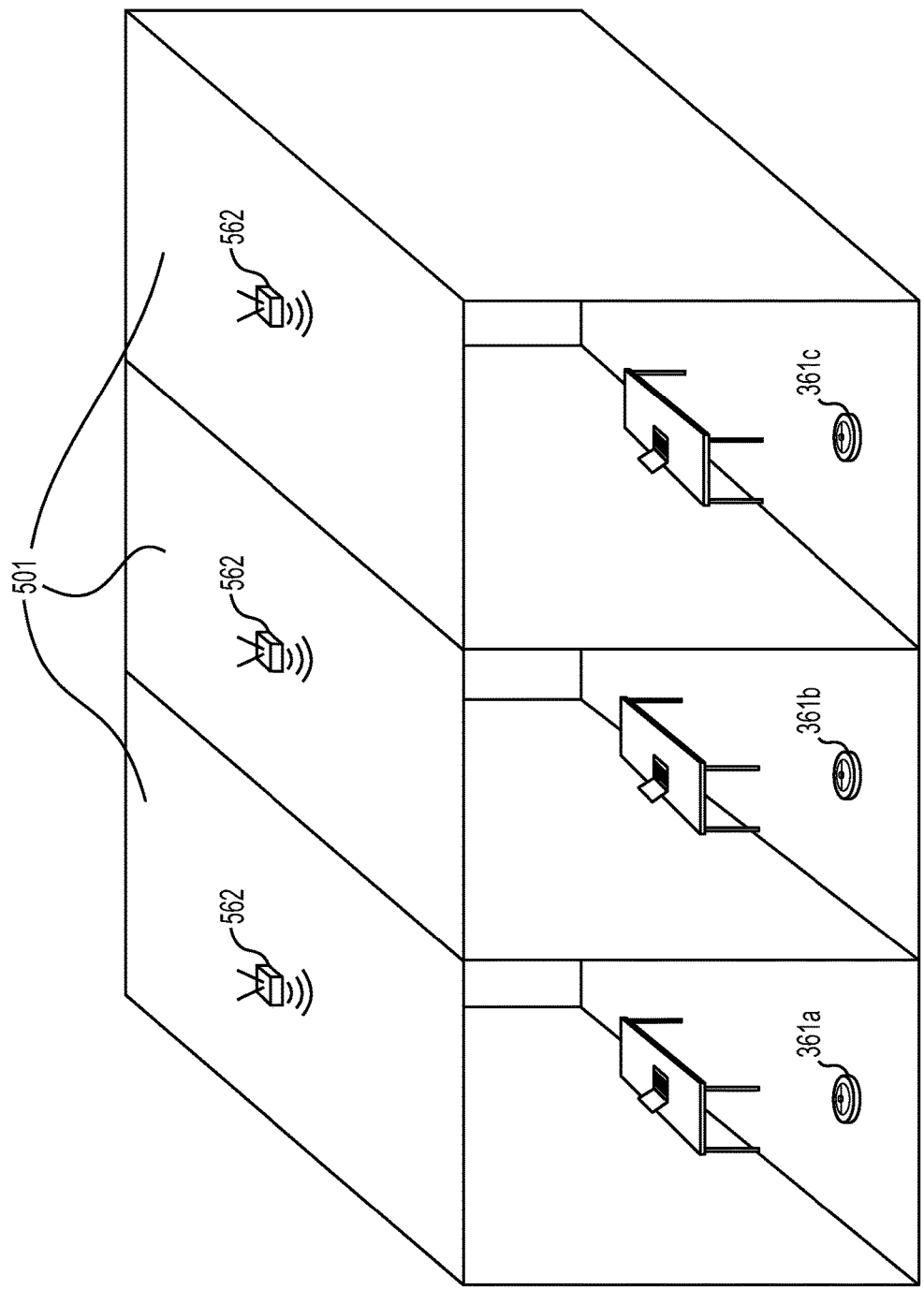
FIGS. 5A and 5B depict an exemplary environment in which a robotic device may be employed, in accordance with an aspect of the present disclosure.
Figure 5B:
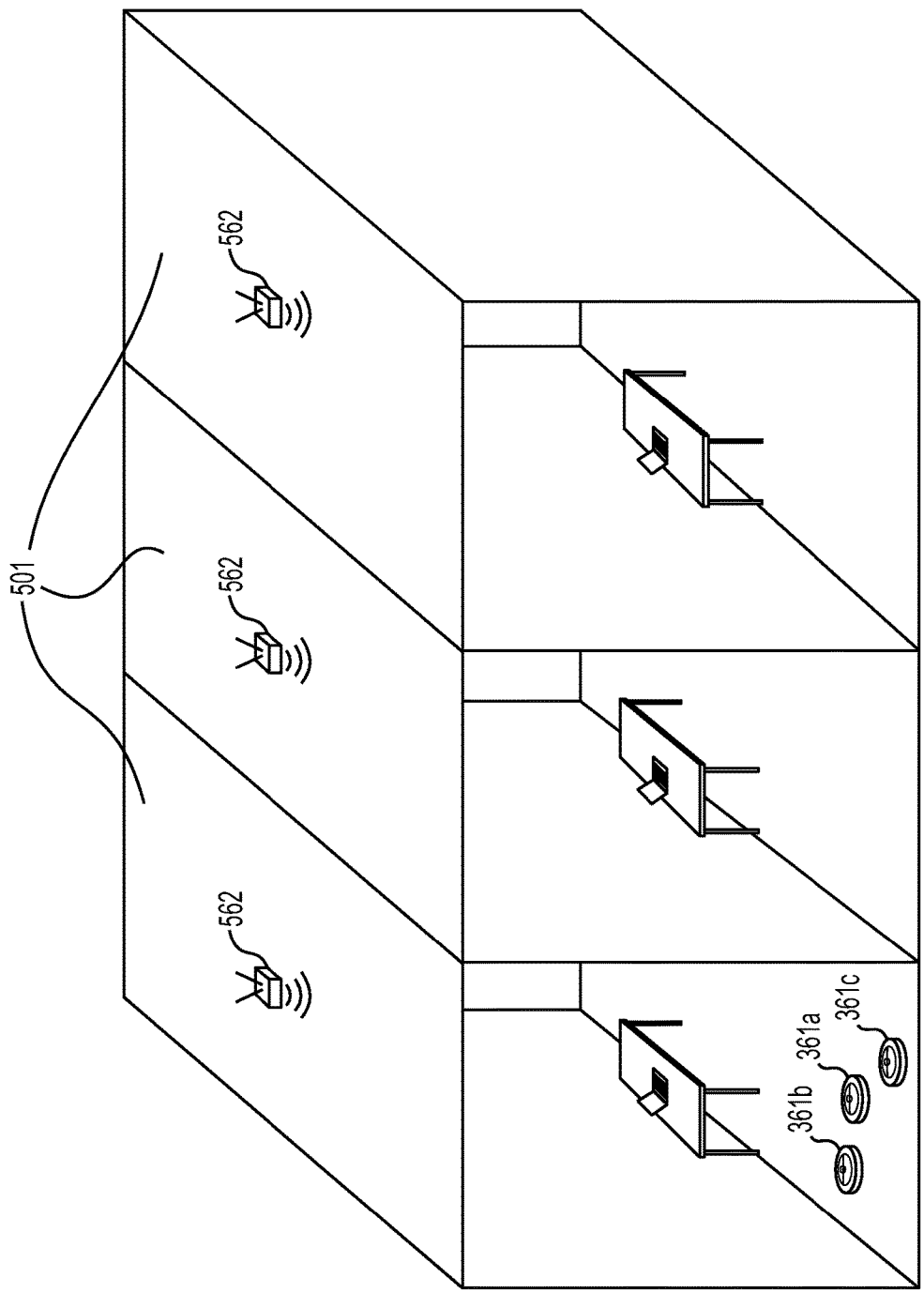

FIG. 5A depicts an exemplary environment in which a robotic device may be employed, in accordance with an aspect of the present disclosure. As illustrated in FIG. 5A, a building may have multiple rooms 501. A swarm of robotic devices 361a, 361b, and 361c may be located across separate rooms as illustrated in FIG. 5A, or they may be located in a same room as illustrated in FIG. 5B. Each of robotic devices 361a, 361b, and 361c may communicate with each other through a communication interface 562. The communication interface 562 may be any device that connects with a network 110 through a wireless network and/or wired network. For example, the communication interface 562 may be a wireless router and/or a gateway 162a, as discussed above with respect to FIGS. 1 and 2.

The swarm of robotic devices 361a, 361b, and 361c may communicate with each other to provide information about the surroundings of each device. For example, if the robotic device 361a detects air impurities and/or floor particles, the robotic device 361a may communicate with other robotic devices (e.g., devices 361b and 361c) through the communication interface 562 to request the robotic devices 361b and 361c initiate their own air purification mode and/or the floor cleaning mode.

Additionally, a robotic device 361a may determine that the room in which it is located has multiple air impurities that may be difficult for robotic device 361a to clean without assistance. This determination may be made by comparing air impurity data obtained through the sensors and cameras with a predetermined threshold. If the air impurities are greater than a predetermined threshold, the robotic device 361a may request assistance from other robotic devices (e.g., devices 361b and 361c). The other robotic devices may then relocate to the room in which robotic device 361a is located, as illustrated in FIG. 5B.

Additionally, the robotic device 361a may determine that the room in which it is located has multiple floor particles that may be difficult for the robotic device 361a to clean without assistance. This determination may be made by comparing floor particle data obtained through the sensors and cameras with a predetermined threshold, and if the floor particles are greater than a predetermined threshold, the robotic device 361a may request assistance from other robotic devices (e.g., devices 361b and 361c). As illustrated in FIG. 5B, the swarm of robotic devices 361b and 361c may travel to assist robotic device 361.

According to one embodiment, a contamination index of a particular room 501 and/or a building (e.g., group of rooms 501) may be determined based on multiple factors, such as an occupancy level, noise, temperature, humidity, and duration of occupants' stay. These factors may be identified using the sensors 301 and the cameras 302 of the robotic devices 361a, 361b, and 361c. The contamination index provides an overall score for a level of contamination of a particular room, office, and/or building.

Additionally, a machine learning algorithm may be used to determine the contamination index. The machine learning algorithm may be a trained policy (e.g., if the machine learning model is trained using a reinforcement learning technique), an analytical model, a neural network, and/or, generally, a model that that takes inputs (e.g., a feature set) and outputs a target (e.g., a target position) based on a trained function. For example, the machine learning algorithm may take several inputs obtained by the sensors and the cameras of the robotic devices, and combine those inputs with external health risk indicators and human resources (HR) information about a number of individuals reporting sick. The machine learning algorithm may then, based on the combination of inputs, identify a contamination risk of a particular area and a time period for which a particular area has a contamination risk higher than a predetermined threshold. According to one embodiment, during periods of highly infectious disease risk and/or after a space has been heavily occupied by occupants (indicating an area has a high potential of contamination risk), a UV-C system may be set to automatically turn on after an area has been unoccupied for a time duration (e.g., based on a system calculated recommendation). Thus, according to one embodiment, the devices and methods of the present disclosure may, using artificial intelligence and machine learning algorithms, automatically disinfect areas that are at high risk of exposing occupants to infectious diseases.

FIG. 6 depicts an exemplary method of operating a robotic device, according to an exemplary embodiment. According to one embodiment, the exemplary method 600 for operating a robotic device may include one or more of the following steps. In step 605, the method includes receiving or obtaining data from one or more sensors and/or one or more cameras of the robotic device. For example, the data may include information obtained from the air quality sensors, proximity sensors, dust sensors, optical sensors, temperature sensors, pressure sensors, photosensors, air pollution sensors, weight measurement sensors, GPS sensors, and/or infrared sensors. The weight measurement sensor may determine an amount of dust and/or garbage that has been collected by the device, and the information may be used to analyze a quality of the air near the device.

In step 610, the method includes detecting, based on the obtained data from the one or more sensors and the one or more cameras, whether air impurities are detected. If air impurities are detected, then the method includes operating an air purification mode of the robotic device (e.g., step 615). The air purification mode includes operating an air filtration system. The air filtration system may include taking air in from the outside through an air intake system and processing the outside air using a HEPA filter system. The clean air is then output into the room. The airflow may be automatically adjusted by changing a flow path of the air using the air filtration system 304.

In step 620, the method includes detecting, based on the obtained data from the one or more sensors and the one or more cameras, whether floor particles are detected. If floor particles are detected, then the method includes operating a floor cleaning mode of the robotic device (e.g., step 625). The floor cleaning mode may include operating the vacuum system and using a weight measurement sensor to determine how much dust and garbage is collected by the robotic device. The vacuum system may also include a rotating brush and a regular filter to clean any dust that has been collected.

In step 630, the method includes updating a status of the device. For example, the processor may continuously obtain data from the one or more sensors and the one or more cameras, and update to a status of the device (e.g., cleaning complete) when there are no air impurities detected and/or no floor particles detected near the robotic device.

In step 635, the method includes transmitting a status of the robotic device to other devices. For example, the data obtained from the sensors and cameras may be transmitted to other robotic devices and/or to a network 110 and/or cloud 105. The data obtained may be transferred to a centralized system to improve an efficiency of air filtration and floor cleaning in other buildings throughout an entire system. Additionally, the obtained data may be collected for use by the EOM 250 to provide a better management of the data and enable improved visualization of the data.

Figure 7:
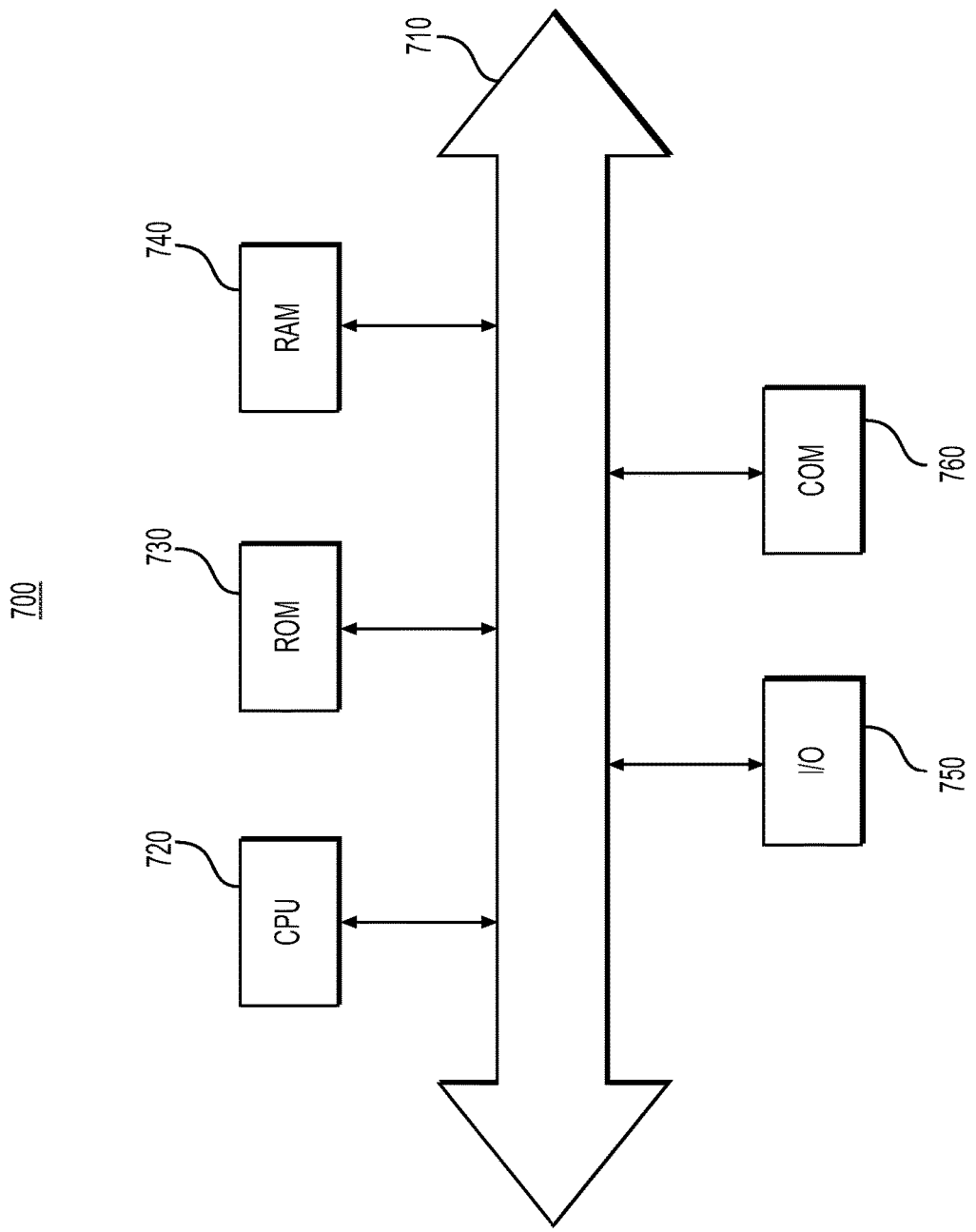
FIG. 7 depicts an example system that may execute techniques presented herein.

FIG. 7 depicts an example system 700 that may execute techniques presented herein. FIG. 7 is a simplified functional block diagram of a computer that may be configured to execute techniques described herein, according to exemplary embodiments of the present disclosure. Specifically, the computer (or "platform" as it may not be a single physical computer infrastructure) may include a data communication interface 760 for packet data communication. The platform also may include a central processing unit ("CPU") 720, in the form of one or more processors, for executing program instructions. The platform may include an internal communication bus 710, and the platform also may include a program storage and/or a data storage for various data files to be processed and/or communicated by the platform such as ROM 730 and RAM 740, although the system 700 may receive programming and data via network communications. The system 700 also may include input and output ports 750 to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

The general discussion of this disclosure provides a brief, general description of a suitable computing environment in which the present disclosure may be implemented. In one embodiment, any of the disclosed systems, methods, and/or graphical user interfaces may be executed by or implemented by a computing system consistent with or similar to that depicted and/or explained in this disclosure. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "server," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure also may be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

'One or more' includes a function being performed by one element, a function being performed by more than one element, e.g., in a distributed fashion, several functions being performed by one element, several functions being performed by several elements, or any combination of the above.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

The terminology used in the description of the various described embodiments herein is for the purpose of describing particular embodiments only and is not intended to be limiting. As used in the description of the various described embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context. INTRODUCTION The systems, apparatuses, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed above should be taken as mandatory for any specific implementation of any of these the apparatuses, devices, systems or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and includes a wide variety of electronic information, including executable code; content such as text, video data, and audio data, among others; and various codes or flags. The terms "information," "data," and "content" are sometimes used interchangeably when permitted by context.

It is intended that the specification and examples be considered as exemplary only, with a true scope and spirit of the disclosure being indicated by the following claims.

What is claimed is:

1. A method, comprising:
    continuously obtaining air purity and floor particle data from one or more sensors and/or one or more cameras of a robotic device among a fleet of robotic devices;
    determining whether air impurities around the robotic device exceed an air purity threshold based on air purity feedback from the one or more sensors of the robotic device;
    based on the determination whether air impurities around the robotic device exceed the air purity threshold, modifying an air purification mode of the robotic device;
    determining whether floor particles around the robotic device exceed a floor particle threshold based on floor particle feedback from the one or more sensors of the robotic device;
    based on the determination whether floor particles around the robotic device exceed the floor particle threshold, modifying a floor cleaning mode of the robotic device; and
    transmitting an operating status of the robotic device to another robotic device in the fleet of robotic devices based on a status of the air purification mode and a status of the floor cleaning mode of the robotic device.

2. The method of claim 1, further comprising transmitting, based on the air impurities around the robotic device exceeding a second air purity threshold based on the air purity feedback from the one or more sensors of the robotic device, a request to a second robotic device in the fleet of robotic devices to modify an air purification mode of the second robotic device.

3. The method of claim 1, further comprising transmitting, based on the floor particles around the robotic device exceeding a second floor particle threshold based on the floor particle feedback from the one or more sensors of the robotic device, a request to a second robotic device in the fleet of robotic devices to modify a floor cleaning mode of the second robotic device.

4. The method of claim 1, further comprising transmitting, based on the air impurities around the robotic device exceeding a second air purity threshold and/or the floor particles around the robotic device exceeding a second floor particle threshold, a request to a second robotic device in the fleet of robotic devices to relocate to a position within a predetermined distance from the robotic device.

5. The method of claim 1, further comprising modifying the air purification mode and the floor cleaning mode simultaneously.

6. The method of claim 1, wherein the modifying the air purification mode comprises automatically adjusting an airflow.

7. The method of claim 1, wherein the modifying the air purification mode comprises initiating, changing, or stopping the air purification mode.

8. The method of claim 1, wherein the modifying the floor cleaning mode comprises initiating, changing, or stopping the floor cleaning mode.

9. The method of claim 1, further comprising transmitting the air purity and floor particle data obtained from the one or more sensors and/or one or more cameras to a second device.

10. The method of claim 9, where the second device is another robotic device.

11. The method of claim 9, wherein the second device is an external server.

12. A system, comprising:
at least one processor; and
at least one memory,
the at least one processor executing instructions to perform operations comprising:
continuously obtaining air purity and floor particle data from one or more sensors and/or one or more cameras of a robotic device among a fleet of robotic devices;
determining whether air impurities around the robotic device exceed an air purity threshold based on air purity feedback from the one or more sensors of the robotic device;
based on the determination whether air impurities around the robotic device exceed the air purity threshold, modifying an air purification mode of the robotic device;
determining whether floor particles around the robotic device exceed a floor particle threshold based on floor particle feedback from the one or more sensors of the robotic device;
based on the determination whether floor particles around the robotic device exceed the floor particle threshold, modifying a floor cleaning mode of the robotic device; and
transmitting an operating status of the robotic device to another robotic device in the fleet of robotic devices based on a status of the air purification mode and a status of the floor cleaning mode of the robotic device.

13. The system of claim 12, wherein the operations further comprise transmitting, based on the air impurities around the robotic device exceeding a second air purity threshold based on the air purity feedback from the one or more sensors of the robotic device, a request to a second robotic device in the fleet of robotic devices to modify an air purification mode of the second robotic device.

14. The system of claim 12, wherein the operations further comprise transmitting, based on the floor particles around the robotic device exceeding a second floor particle threshold based on the floor particle feedback from the one or more sensors of the robotic device, a request to a second robotic device in the fleet of robotic devices to modify a floor cleaning mode of the second robotic device.

15. The system of claim 12, wherein the operations further comprise transmitting, based on the air impurities around the robotic device exceeding a second air purity threshold and/or the floor particles around the robotic device exceeding a second floor particle threshold, a request to a second robotic device in the fleet of robotic devices to relocate to a position within a predetermined distance from the robotic device.

16. The system of claim 12, wherein the operations further comprise modifying the floor cleaning mode comprises initiating, changing, or stopping the floor cleaning mode.

17. A non-transitory computer-readable storage medium storing instructions that, when executed by at least one processor, cause the at least one processor to perform a method of:
continuously obtaining air purity and floor particle data from one or more sensors and/or one or more cameras of a robotic device among a fleet of robotic devices;
determining whether air impurities around the robotic device exceed an air purity threshold based on air purity feedback from the one or more sensors of the robotic device;
based on the determination whether air impurities around the robotic device exceed the air purity threshold, modifying an air purification mode of the robotic device;
determining whether floor particles around the robotic device exceed a floor particle threshold based on floor particle feedback from the one or more sensors of the robotic device;
based on the determination whether floor particles around the robotic device exceed the floor particle threshold, modifying a floor cleaning mode of the robotic device; and
transmitting an operating status of the robotic device to another robotic device in the fleet of robotic devices based on a status of the air purification mode and a status of the floor cleaning mode of the robotic device.

18. The non-transitory computer-readable storage medium of claim 17, the method further comprising transmitting, based on the air impurities around the robotic device exceeding a second air purity threshold based on the air purity feedback from the one or more sensors of the robotic device, a request to a second robotic device in the fleet of robotic devices to modify an air purification mode of the second robotic device.

19. The non-transitory computer-readable storage medium of claim 17, the method further comprising transmitting, based on the floor particles around the robotic device exceeding a second floor particle threshold based on the floor particle feedback from the one or more sensors of the robotic device, a request to a second robotic device in the fleet of robotic devices to modify a floor cleaning mode of the second robotic device.

20. The non-transitory computer-readable storage medium of claim 17, the method further comprising transmitting, based on the air impurities around the robotic device exceeding a second air purity threshold and/or the floor particles around the robotic device exceeding a second floor particle threshold, a request to a second robotic device in the fleet of robotic devices to relocate to a position within a predetermined distance from the robotic device.

\* \* \* \* \*